(12) United States Patent
Ben-Tsur

(10) Patent No.: US 11,638,678 B1
(45) Date of Patent: May 2, 2023

(54) VIBRATING CAPSULE SYSTEM AND TREATMENT METHOD

(71) Applicant: VIBRANT LTD., Yokneam (IL)

(72) Inventor: Lior Ben-Tsur, Netanya (IL)

(73) Assignee: Vibrant Ltd., Yokneam (IL)

( * ) Notice: Subject to any disclaimer, the term of this patent is extended or adjusted under 35 U.S.C. 154(b) by 851 days.

(21) Appl. No.: 16/377,213

(22) Filed: Apr. 7, 2019

Related U.S. Application Data

(60) Provisional application No. 62/654,538, filed on Apr. 9, 2018.

(51) Int. Cl.
*A61H 23/02* (2006.01)
*A61B 5/07* (2006.01)
*A61B 5/00* (2006.01)

(52) U.S. Cl.
CPC ............ *A61H 23/02* (2013.01); *A61B 5/073* (2013.01); *A61B 5/6861* (2013.01); *A61H 2201/1207* (2013.01); *A61H 2201/5097* (2013.01)

(58) Field of Classification Search
CPC .......... A61H 1/00; A61H 23/00; A61H 23/02; A61H 23/0254; A61H 23/0263; A61H 2201/1207; A61H 2205/083; A61H 21/00; A61B 5/6861; A61B 5/073
See application file for complete search history.

(56) References Cited

U.S. PATENT DOCUMENTS

| | | |
|---|---|---|
| 3,485,235 A | 12/1969 | Felson |
| 4,239,040 A | 12/1980 | Hosoya et al. |
| 4,507,115 A | 3/1985 | Kambara et al. |
| 5,170,801 A | 12/1992 | Casper et al. |
| 5,991,931 A | 11/1999 | Hawkins et al. |
| 6,453,199 B1 | 9/2002 | Kobozev |
| 6,632,216 B2 | 10/2003 | Houzego et al. |
| 6,687,537 B2 | 2/2004 | Bernabei |

(Continued)

FOREIGN PATENT DOCUMENTS

| | | |
|---|---|---|
| CN | 1829466 A | 9/2006 |
| CN | 101810481 A | 8/2010 |

(Continued)

OTHER PUBLICATIONS

CN101810481 Machine Translation (by Google Translate)—published Aug. 25, 2010.

(Continued)

*Primary Examiner* — Joseph D. Boecker
*Assistant Examiner* — Thomas W Greig
(74) *Attorney, Agent, or Firm* — Momentum IP; Marc Van Dyke

(57) ABSTRACT

A vibrating gastrointestinal capsule and method of use thereof for treating Parkinsonism in a subject, the method including: (a) providing a vibrating gastrointestinal capsule having a housing; a vibrating agitation mechanism adapted such that, in a vibrating mode of operation, the housing exerts vibrations on an environment surrounding the capsule; and a power supply disposed within the housing and adapted to power the vibrating agitation mechanism; (b) ingesting the capsule, by the subject; and (c) controlling the vibrating agitation mechanism such that at least a portion of the vibrating mode of operation occurs within the stomach and/or the small intestine of the subject.

18 Claims, 2 Drawing Sheets

(56) References Cited

U.S. PATENT DOCUMENTS

| | | |
|---|---|---|
| 6,776,165 B2 | 8/2004 | Jin |
| 6,911,004 B2 | 6/2005 | Kim et al. |
| 6,929,363 B2 | 8/2005 | Sakai et al. |
| 6,984,205 B2 | 1/2006 | Gazdzinski |
| 7,076,284 B2 | 7/2006 | Segawa et al. |
| 7,354,397 B2 | 4/2008 | Fujita et al. |
| 7,510,537 B2 | 3/2009 | Imboden et al. |
| 7,511,733 B2 | 3/2009 | Takizawa et al. |
| 7,623,904 B2 | 11/2009 | Uchiyama et al. |
| 7,637,864 B2 | 12/2009 | Yokoi et al. |
| 7,686,788 B2 | 3/2010 | Freyman et al. |
| 7,797,033 B2 | 9/2010 | DAndrea et al. |
| 7,942,811 B2 | 5/2011 | Segawa et al. |
| 8,021,356 B2 | 9/2011 | Uchiyama et al. |
| 8,021,357 B2 | 9/2011 | Tanaka et al. |
| 8,021,384 B2 | 9/2011 | Weiss et al. |
| 8,036,748 B2 | 10/2011 | Zdeblick et al. |
| 8,038,600 B2 | 10/2011 | Uchiyama et al. |
| 8,147,482 B2 | 4/2012 | Shimizu et al. |
| 8,202,697 B2 | 6/2012 | Holmes |
| 8,216,130 B2 | 7/2012 | Glukhovsky et al. |
| 8,295,932 B2 | 10/2012 | Bitton et al. |
| 8,306,592 B2 | 11/2012 | Takizawa et al. |
| 8,518,022 B2 | 8/2013 | Trovato et al. |
| 8,597,278 B2 | 12/2013 | Trovato et al. |
| 8,701,677 B2 | 4/2014 | Duan et al. |
| 8,755,888 B2 | 6/2014 | Voznesensky et al. |
| 8,771,730 B2 | 7/2014 | Navon et al. |
| 8,852,172 B2 | 10/2014 | Dijksman et al. |
| 8,945,005 B2 | 2/2015 | Hafezi et al. |
| 9,078,799 B2 | 7/2015 | Shohat et al. |
| 9,156,169 B2 | 10/2015 | Duan et al. |
| 9,232,909 B2 | 1/2016 | Duan et al. |
| 9,511,211 B2 | 12/2016 | Tange et al. |
| 9,532,923 B2 | 1/2017 | Shohat et al. |
| 9,538,937 B2 | 1/2017 | Rohde et al. |
| 9,572,746 B2 | 2/2017 | Asfora |
| 9,707,150 B2 | 7/2017 | Shabbat |
| 9,730,336 B2 | 8/2017 | Arneson et al. |
| 9,750,923 B2 | 9/2017 | Niichel et al. |
| 9,770,588 B2 | 9/2017 | Bettinger |
| 9,919,152 B2 | 3/2018 | Levine et al. |
| 9,986,898 B2 | 6/2018 | Duan et al. |
| 9,999,415 B2 | 6/2018 | Duan et al. |
| 10,070,854 B2 | 9/2018 | Duan et al. |
| 10,076,234 B2 | 9/2018 | Duan et al. |
| 10,118,035 B2 | 11/2018 | Perez et al. |
| 10,143,364 B2 | 12/2018 | Duan et al. |
| 10,172,598 B2 | 1/2019 | Amoako-Tuffour et al. |
| 10,314,514 B2 | 6/2019 | Duan |
| 10,369,463 B2 | 8/2019 | Barney et al. |
| 10,478,047 B2 | 11/2019 | Duan et al. |
| 10,478,373 B2 | 11/2019 | Duan et al. |
| 10,500,127 B2 | 12/2019 | Duan et al. |
| 10,517,466 B2 | 12/2019 | Ye et al. |
| 10,531,788 B2 | 1/2020 | Wang et al. |
| 10,537,720 B2 | 1/2020 | Ben-Tsur |
| 10,543,348 B2 | 1/2020 | Ben-Tsur |
| 10,869,811 B2 | 12/2020 | Duan et al. |
| 10,874,339 B2 | 12/2020 | Chavan et al. |
| 10,888,277 B1 | 1/2021 | Ben-Tsur et al. |
| 10,905,378 B1 | 2/2021 | Ben-Tsur et al. |
| 2002/0055734 A1 | 5/2002 | Houzego et al. |
| 2002/0099310 A1 | 7/2002 | Kimchy et al. |
| 2002/0103417 A1 | 8/2002 | Gazdzinski |
| 2002/0132226 A1 | 9/2002 | Nair et al. |
| 2002/0147466 A1* | 10/2002 | Bernabei ............ A61N 1/0424 607/3 |
| 2003/0020810 A1 | 1/2003 | Takizawa et al. |
| 2003/0073935 A1 | 4/2003 | Segawa et al. |
| 2003/0191430 A1 | 10/2003 | DAndrea et al. |
| 2004/0030454 A1 | 2/2004 | Kim et al. |
| 2004/0050394 A1 | 3/2004 | Jin |
| 2004/0253304 A1 | 12/2004 | Gross et al. |
| 2004/0267240 A1 | 12/2004 | Gross et al. |
| 2005/0058701 A1 | 3/2005 | Gross et al. |
| 2005/0085696 A1 | 4/2005 | Uchiyama et al. |
| 2005/0148847 A1 | 7/2005 | Uchiyama et al. |
| 2005/0177069 A1 | 8/2005 | Takizawa et al. |
| 2006/0062852 A1 | 3/2006 | Holmes |
| 2006/0094992 A1 | 5/2006 | Imboden et al. |
| 2006/0169293 A1 | 8/2006 | Yokoi et al. |
| 2006/0200083 A1 | 9/2006 | Freyman et al. |
| 2006/0211963 A1 | 9/2006 | Spirk et al. |
| 2006/0270899 A1 | 11/2006 | Amirana |
| 2006/0276729 A1 | 12/2006 | Reed et al. |
| 2007/0015952 A1 | 1/2007 | Chang et al. |
| 2007/0032699 A1 | 2/2007 | Segawa et al. |
| 2007/0123809 A1 | 5/2007 | Weiss et al. |
| 2007/0213659 A1* | 9/2007 | Trovato ............ A61M 31/002 604/48 |
| 2007/0238940 A1* | 10/2007 | Amirana ............ A61B 5/4839 600/302 |
| 2007/0299301 A1 | 12/2007 | Uchiyama et al. |
| 2008/0051635 A1 | 2/2008 | Tanaka et al. |
| 2008/0065168 A1 | 3/2008 | Bitton et al. |
| 2008/0161639 A1 | 7/2008 | Katayama et al. |
| 2008/0188837 A1 | 8/2008 | Belsky et al. |
| 2008/0269664 A1 | 10/2008 | Trovato et al. |
| 2008/0275430 A1 | 11/2008 | Belsky et al. |
| 2008/0281238 A1 | 11/2008 | Oohashi et al. |
| 2009/0043278 A1 | 2/2009 | Tanaka et al. |
| 2009/0275923 A1 | 11/2009 | Shimizu et al. |
| 2009/0281380 A1 | 11/2009 | Miller et al. |
| 2009/0306632 A1 | 12/2009 | Trovato et al. |
| 2009/0306633 A1 | 12/2009 | Trovato et al. |
| 2009/0318783 A1 | 12/2009 | Rohde et al. |
| 2009/0318841 A1* | 12/2009 | Shohat ............ A61H 23/02 601/46 |
| 2010/0039616 A1 | 2/2010 | Yumikake et al. |
| 2010/0049012 A1 | 2/2010 | Dijksman et al. |
| 2010/0217079 A1 | 8/2010 | Tichy |
| 2010/0222670 A1 | 9/2010 | Demierre et al. |
| 2010/0312228 A1 | 12/2010 | Zdeblick et al. |
| 2010/0324381 A1 | 12/2010 | Glukhovsky et al. |
| 2011/0117192 A1 | 5/2011 | Navon et al. |
| 2011/0208011 A1 | 8/2011 | Ben-Horin |
| 2011/0240044 A1 | 10/2011 | Duan et al. |
| 2011/0319727 A1 | 12/2011 | Ishihara |
| 2013/0046150 A1* | 2/2013 | Devanaboyina ....... A61B 5/369 600/382 |
| 2013/0158452 A1 | 6/2013 | Juto et al. |
| 2013/0213495 A1 | 8/2013 | Huang et al. |
| 2013/0253387 A1 | 9/2013 | Bonutti et al. |
| 2013/0267788 A1 | 10/2013 | Duan et al. |
| 2014/0107726 A1 | 4/2014 | Voznesensky et al. |
| 2014/0187907 A1 | 7/2014 | Duan et al. |
| 2014/0221741 A1 | 8/2014 | Wang et al. |
| 2014/0247039 A1 | 9/2014 | Duan et al. |
| 2014/0288470 A1 | 9/2014 | Asfora |
| 2015/0011829 A1 | 1/2015 | Wang et al. |
| 2015/0011874 A1 | 1/2015 | Amoako-Tuffour et al. |
| 2015/0018614 A1 | 1/2015 | Duan et al. |
| 2015/0018615 A1 | 1/2015 | Duan et al. |
| 2015/0045658 A1 | 2/2015 | Tange et al. |
| 2015/0065926 A1 | 3/2015 | Nakamura et al. |
| 2015/0073315 A1* | 3/2015 | Shabbat ............ A61H 23/02 601/46 |
| 2015/0088222 A1 | 3/2015 | Bettinger |
| 2015/0223727 A1 | 8/2015 | Kimchy et al. |
| 2015/0313792 A1 | 11/2015 | Shohat et al. |
| 2015/0380140 A1 | 12/2015 | Duan et al. |
| 2016/0121111 A1 | 5/2016 | Levine et al. |
| 2016/0136104 A1* | 5/2016 | Niichel ............ A61K 41/0028 424/452 |
| 2016/0183878 A1 | 6/2016 | Weast et al. |
| 2016/0287058 A1 | 10/2016 | Ye et al. |
| 2016/0303133 A1 | 10/2016 | Dudley et al. |
| 2016/0310357 A1 | 10/2016 | Duan et al. |
| 2017/0001003 A1* | 1/2017 | Pivonka ............ A61B 5/4836 |
| 2017/0020374 A1 | 1/2017 | Duan et al. |
| 2017/0021172 A1 | 1/2017 | Perez et al. |
| 2017/0035407 A1 | 2/2017 | Duan et al. |
| 2017/0035520 A1 | 2/2017 | Duan et al. |

(56) References Cited

U.S. PATENT DOCUMENTS

| | | | |
|---|---|---|---|
| 2017/0135897 A1 | 5/2017 | Shohat et al. | |
| 2017/0151423 A1 | 6/2017 | Vandierendonck et al. | |
| 2017/0273863 A1 | 9/2017 | Shabbat | |
| 2017/0296425 A1 | 10/2017 | Duan et al. | |
| 2017/0296428 A1* | 10/2017 | Duan | A61H 23/0263 |
| 2017/0340242 A1 | 11/2017 | Duan | |
| 2018/0055597 A1 | 3/2018 | Duan et al. | |
| 2018/0084975 A1 | 3/2018 | Duan et al. | |
| 2018/0168490 A1 | 6/2018 | Jones et al. | |
| 2018/0185238 A1 | 7/2018 | Ilan | |
| 2018/0360355 A1 | 12/2018 | Chavan et al. | |
| 2019/0224070 A1 | 7/2019 | Ben-Tsur et al. | |
| 2019/0307999 A1 | 10/2019 | Ben-Tsur | |
| 2019/0308002 A1 | 10/2019 | Ben-Tsur | |
| 2020/0315541 A1 | 10/2020 | Ben-Tsur et al. | |

FOREIGN PATENT DOCUMENTS

| | | |
|---|---|---|
| CN | 102743174 A | 10/2012 |
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105380777 A | 3/2016 |
| CN | 105411505 A | 3/2016 |
| CN | 205108749 U | 3/2016 |
| CN | 205286889 U | 6/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2002163359 A | 6/2002 |
| JP | 2005052502 A | 3/2005 |
| JP | 2010503451 A | 2/2010 |
| JP | 2010246703 A | 11/2010 |
| JP | 2013535756 A | 9/2013 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

CN102743174 Machine Translation (by Google Translate)—published Jun. 29, 2016.
CN102743175 Machine Translation (by Google Translate—published Oct. 24, 2012.
CN102743176A Machine Translation (by Google Translate)—published Oct. 24, 2012.
CN102813515 Machine Translation (by Google Translate)—published Dec. 12, 2012.
CN102860810 Machine Translation (by Google Translate)—published Oct. 29, 2014.
CN104898850 Machine Translation (by Google Translate)—published Feb. 6, 2018.
CN 103222842 Machine Translation (by Google Translate)—Sep. 9, 2015.
CN105025245 Machine Translation (by Google Translate)—published Nov. 4, 2015.
CN105079970 Machine Translation (by Google Translate)—published Jun. 19, 2018.
CN105380777 Machine Translation (by Google Translate)—published Oct. 27, 2017.
CN105411505 Machine Translation (by Google Translate)—published Aug. 23, 2019.
CN105939451 Machine Translation (by Google Translate)—published Oct. 2, 2018.
CN105942959 Machine Translation (by Google Translate)—published Aug. 24, 2018.
CN105996961 Machine Translation (by Google Translate)—published May 11, 2018.
CN106056588 Machine Translation (by Google Translate)—published Oct. 26, 2016.
CN106137760 Machine Translation (by Google Translate)—published Nov. 23, 2016.
CN106097335B Machine Translation (by Google Translate)—published Jan. 25, 2019.
CN106204599B Machine Translation (by Google Translate)—published Apr. 26, 2019.
CN106373137 Machine Translation (by Google Translate)—published Jan. 4, 2019.
CN106923787 Machine Translation (by Google Translate)—published Jul. 7, 2017.
CN106934799 Machine Translation (by Google Translate)—published Sep. 3, 2019.
CN107174188 Machine Translation (by Google Translate)—published Sep. 19, 2017.
CN107233580 Machine Translation (by Google Translate)—published Mar. 2, 2021.
CN107240091 Machine Translation (by Google Translate)—published Sep. 3, 2019.
CN107375951B Machine Translation (by Google Translate)—published Apr. 2, 2021.
CN1829466B Machine Translation (by Google Translate)—published Jan. 5, 2011.
CN202483565 Machine Translation (by Google Translate)—published Oct. 10, 2012.
CN202699138 Machine Translation (by Google Translate)—published Jan. 30, 2013.
CN202821355 Machine Translation (by Google Translate)—published Mar. 27, 2013.
CN202843564 Machine Translation (by Google Translate)—published Apr. 3, 2013.
CN202843608 Machine Translation (by Google Translate)—published Apr. 3, 2013.
CN202875332 Machine Translation (by Google Translate)—published Apr. 17, 2013.
CN203634116 Machine Translation (by Google Translate)—published Jun. 11, 2014.
CN205108749 Machine Translation (by Google Translate)—published Mar. 30, 2016
CN205286889 Machine Translation (by Google Translate)—published Jun. 8, 2016.
CN205758500 Machine Translation (by Google Translate)—published Dec. 7, 2016.

(56) References Cited

OTHER PUBLICATIONS

CN205913317 Machine Translation (by Google Translate)—published Feb. 1, 2017.
CN205928774 Machine Translation (by Google Translate)—published Feb. 8, 2017.
JP2001062397 Machine Translation (by Google Translate)—published Mar. 13, 2001.
JP2002163359A Machine Translation (by Google Translate)—published Jun. 7, 2002.
JP2005052502 Machine Translation (by Google Translate)—published Aug. 10, 2006.
JP2010246703 Machine Translation (by Google Translate)—published Nov. 4, 2010.
JP2010503451 Machine Translation (by Google Translate)—published Nov. 21, 2012.
JP2013535756 Machine Translation (by Google Translate)—published Sep. 25, 2014.
Processing of Polymer Matrix Composites Containing CNTs Dec. 1, 2015 by Marcio Loos (Federal University of Santa Catarina).
Comparison of pharmacokinetic profile of levodopa throughout the day between levodopa/carbidopa/entacapone and levodopa/carbidopa when administered four or five times daily Mar. 1, 2009 European Journal of Clinical Pharmacology 65(5):443-55 Kuoppamäki et al.

* cited by examiner

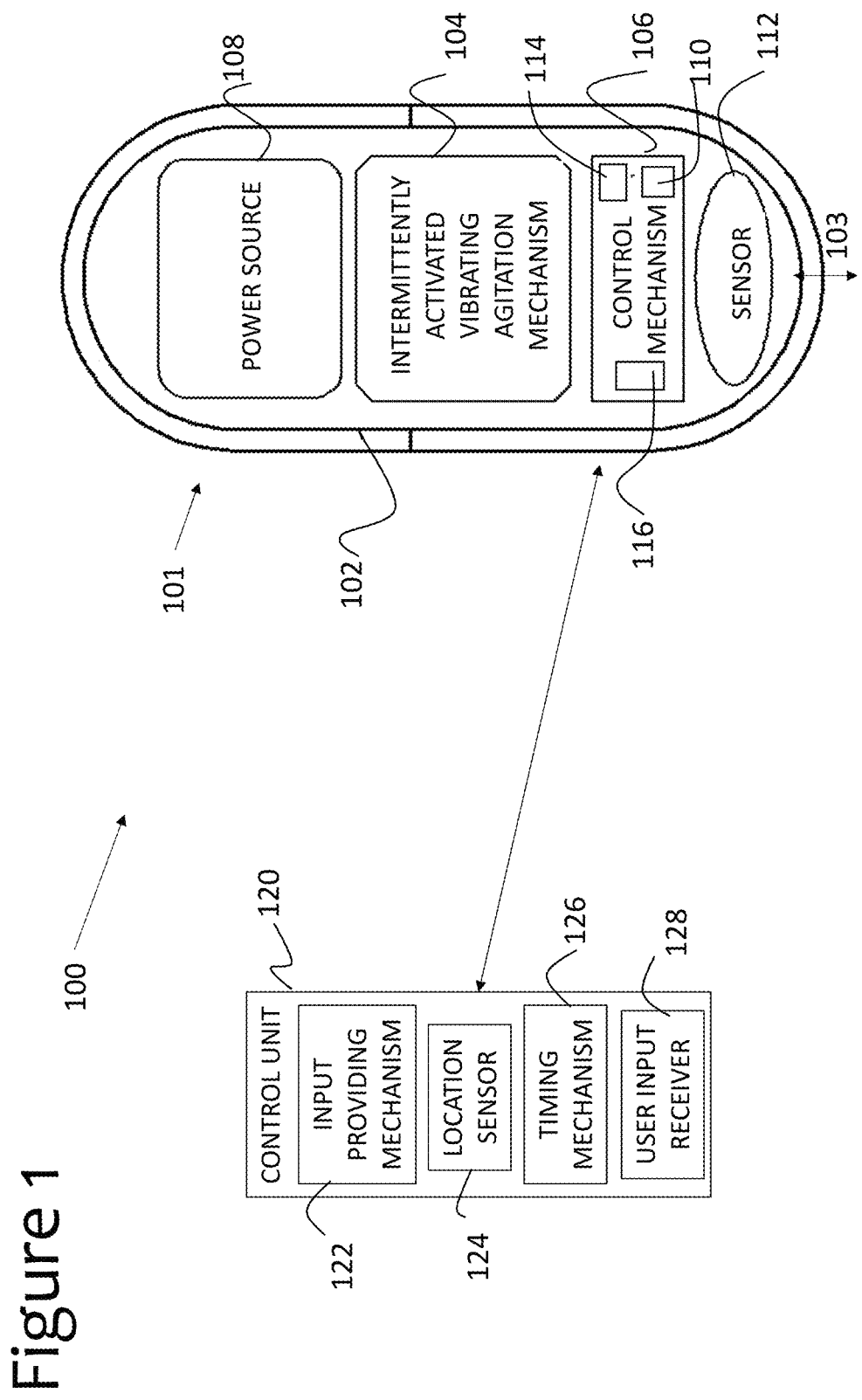

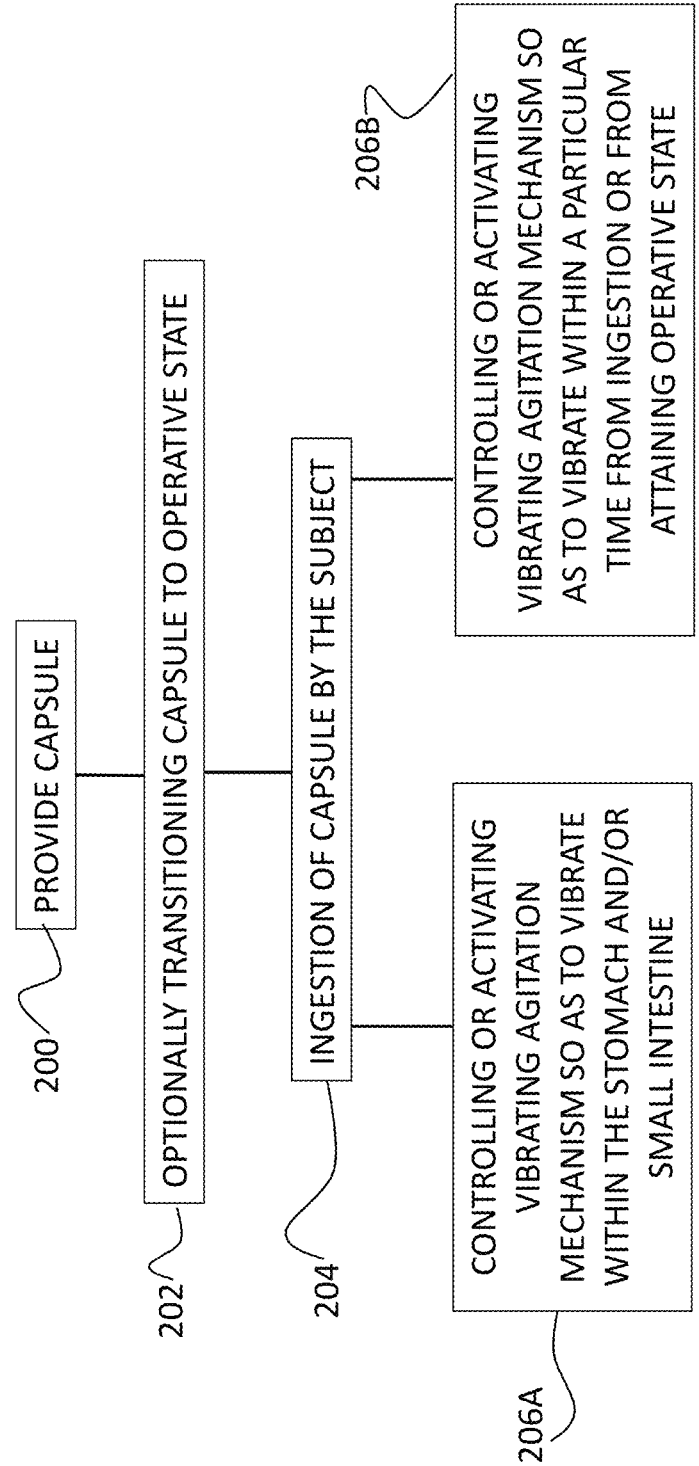

VIBRATING CAPSULE SYSTEM AND TREATMENT METHOD

RELATED APPLICATIONS

The present application gains priority from U.S. Provisional Patent Application No. 62/654,538 filed Apr. 9, 2018 and entitled VIBRATING CAPSULE SYSTEM AND TREATMENT METHOD, which is incorporated herein by reference as if fully set forth herein.

FIELD OF THE INVENTION

The present invention relates in general to vibrating capsule systems including one or more vibrating capsules, and to treatment methods using such systems and capsules, and more particularly, to vibrating capsule systems and methods for treating Parkinsonism, including Parkinson's Disease.

SUMMARY OF THE INVENTION

In accordance with an embodiment of the present invention, there is provided a method of using a vibrating gastrointestinal capsule in the treatment of Parkinsonism in a subject, the method including:
(a) providing the vibrating gastrointestinal capsule, the vibrating gastrointestinal capsule having:
  a housing;
  a vibrating agitation mechanism adapted such that, in a first vibrating mode of operation, the housing exerts vibrations on an environment surrounding the vibrating gastrointestinal capsule; and
  a power supply disposed within the housing and adapted to power the vibrating agitation mechanism;
(b) ingesting the vibrating gastrointestinal capsule, by the subject;
(c) controlling or activating the vibrating agitation mechanism such that at least a portion of the first vibrating mode of operation occurs within a portion of a gastrointestinal tract of the subject, the portion consisting at most of a stomach, a small intestine, and large intestine.

In some embodiments, the portion of the gastrointestinal tract consists at most of the stomach and the small intestine. In some such embodiments, the portion of the gastrointestinal tract consists of the stomach. In other such embodiments, the portion of the gastrointestinal tract consists of the small intestine.

In some embodiments, the vibrating gastrointestinal capsule is adapted and/or dimensioned to transit the gastrointestinal tract.

In some embodiments, the vibrating gastrointestinal capsule includes, or is associated with, a control mechanism adapted to activate the vibrating agitation mechanism to operate in the first vibrating mode of operation.

In some embodiments, the treatment of Parkinsonism is, or includes, delaying an onset of Parkinsonism. In some embodiments, the treatment of Parkinsonism is, or includes, mitigating or retarding a development of Parkinsonism.

In some embodiments, the treatment of Parkinsonism is, or includes, managing a condition of Parkinsonism. In some embodiments, managing a condition of Parkinsonism includes effecting an increased absorption of a medicament used in the treatment of the Parkinsonism, thereby improving a therapeutic efficacy of the medicament. In some embodiments, managing a condition of Parkinsonism includes effecting an increased absorption of a medicament used in the treatment of the Parkinsonism, thereby enabling the use of a lower dosage of the medicament, optionally without impairing or diminishing therapeutic efficacy.

In some embodiments, the treatment of Parkinsonism is the treatment of Parkinson's disease.

In some embodiments, the first vibrating mode of operation is effected within the portion of the gastrointestinal tract so as to stimulate the enteric nervous system of the subject.

In some embodiments, the first vibrating mode of operation is effected within the portion of the gastrointestinal tract so as to induce at least one peristaltic wave in a wall of the gastrointestinal tract.

In some embodiments, the first vibrating mode of operation is effected within the portion of the gastrointestinal tract so as to increase peristalsis in a wall of the gastrointestinal tract. In some embodiments, the increasing of the peristalsis is effected so as to stimulate the enteric nervous system of the subject.

In some embodiments, the method further includes diagnosing a pre-disposition to Parkinsonism or Parkinson's disease in the subject, wherein the treatment of Parkinsonism is, or includes, delaying an onset of Parkinsonism.

In some embodiments, the method further includes timing at least one of the ingesting of the vibrating gastrointestinal capsule and the activating of the vibrating agitation mechanism such that the first vibrating mode of operation occurs during an absorption time of an ingested medicament within the gastrointestinal tract of the subject. In some embodiments, the absorption time is an estimated absorption time. In some embodiments, the absorption time is an actual absorption time.

In some embodiments, the timing is effected such that the ingesting of the vibrating gastrointestinal capsule transpires within 5 hours, within 4 hours, within 3.5 hours, within 3 hours, within 2.5 hours, within 2 hours, within 1.5 hours, within 1 hour, or within 0.5 hours of the ingesting of the medicament.

In some embodiments, the medicament includes a substance for treating Parkinsonism or Parkinson's disease. In some embodiments, the medicament includes at least one dopaminergic agent. In some embodiments, the medicament includes at least one catecholamine precursor. In some embodiments, the at least one catecholamine precursor includes a dopamine precursor. In some embodiments, the dopamine precursor includes at least one dopamine precursor agent such as (L)-3,4-dihydroxyphenylalanine. In some embodiments, the medicament includes N-methyl-N-(2-propynyl)-2-methyl-1-phenylethyl-2-amine.

In some embodiments, the capsule further includes a control mechanism adapted, in response to receipt of an activation input, to activate the vibrating agitation mechanism to operate in the first vibrating mode of operation.

In some embodiments, the capsule further includes at least one sensor adapted to provide the activation input.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor and the receiving the at least one activation input includes receiving input indicting pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the receipt of the activation input includes receiving the activation input from a control unit remote from the gastrointestinal capsule.

In some embodiments, the receiving the activation input includes receiving the activation input following the ingesting.

In some embodiments, the receiving the activation input includes receiving the activation input prior to the ingesting.

In some embodiments, the receiving the activation input additionally includes receiving a vibration protocol to be used by the control mechanism to control operation of the vibrating agitation mechanism.

In some embodiments, the vibrating agitation mechanism includes at least a radial agitation mechanism, and the controlling includes controlling the radial agitation mechanism, in the first vibrating mode of operation, to exert radial forces on the housing, in a radial direction with respect to a or the longitudinal axis of the housing, thereby to cause the vibrations exerted by the housing.

In some embodiments, the vibrating agitation mechanism includes at least an axial agitation mechanism, and wherein the control mechanism is adapted to control the axial agitation mechanism, in the first vibrating mode of operation, to exert axial forces on the housing, in an axial direction with respect to a or the longitudinal axis of the housing, thereby to cause the vibrations exerted by the housing.

In some embodiments, the control mechanism is adapted to control the vibrating agitation mechanism, in the first vibrating mode of operation, to exert radial forces on the housing in a radial direction with respect to a or the longitudinal axis of the housing and to exert axial forces on the housing in an axial direction with respect to a or the longitudinal axis of the housing, thereby to cause the vibrations exerted by the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the control mechanism is adapted to control the vibrating agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control mechanism is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitation mechanism is configured such that a net force exerted by the housing on the environment is in the range of 50 grams-force to 600 grams-force.

In some embodiments, in the first vibration mode of operation the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the activating the vibrating agitation mechanism is effected such that at least a portion of the first vibrating mode of operation occurs within 6 hours, within 5 hours, within 4.5 hours, within 4 hours, within 3.5 hours, within 3 hours, within 2.5 hours, within 2 hours, within 1.5 hours, within 1 hour, or within 0.5 hours of the ingesting.

In accordance with another embodiment of the present invention, there is provided a vibrating gastrointestinal capsule for use in the treatment of Parkinsonism in a subject, the capsule including:
  (a) a housing;
  (b) a vibrating agitation mechanism adapted such that, in a first vibrating mode of operation, the housing exerts vibrations on an environment surrounding the vibrating gastrointestinal capsule; and
  (c) a power supply disposed within the housing and adapted to power the vibrating agitation mechanism.

In some embodiments, the capsule further includes at least one of the structural features as described hereinabove.

In accordance with a further embodiment of the present invention, there is provided a method of using a vibrating gastrointestinal capsule in the treatment of Parkinsonism in a subject, the method including:
(a) providing the vibrating gastrointestinal capsule, the vibrating gastrointestinal capsule having:
  a housing;
  a vibrating agitation mechanism adapted such that, in a first vibrating mode of operation, the housing exerts vibrations on an environment surrounding the vibrating gastrointestinal capsule; and a power supply disposed within the housing and adapted to power the vibrating agitation mechanism;

(b) ingesting the vibrating gastrointestinal capsule, by the subject;

(c) activating the vibrating agitation mechanism such that at least a portion of the first vibrating mode of operation occurs within 6 hours, within 5 hours, within 4.5 hours, within 4 hours, within 3.5 hours, within 3 hours, within 2.5 hours, within 2 hours, within 1.5 hours, within 1 hour, or within 0.5 hours of the ingesting of the vibrating gastrointestinal capsule.

BRIEF DESCRIPTION OF THE FIGURES

The foregoing discussion will be understood more readily from the following detailed description of the invention, when taken in conjunction with the accompanying FIGS. 1-2), in which:

FIG. 1 is a schematic block diagram of a gastrointestinal treatment system including a vibrating ingestible capsule according to an embodiment of the present invention; and FIG. 2 is a schematic flowchart of a method for using a vibrating gastrointestinal capsule in the treatment of Parkinsonism, according to the present invention, the treatment being based on use of an ingestible vibrating gastrointestinal capsule, for example as shown in FIG. 1.

DESCRIPTION OF THE PREFERRED EMBODIMENTS

The principles of the inventive gastrointestinal treatment system and method of using the inventive gastrointestinal treatment system in treatment of Parkinsonism, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "subject" relates to a human.

For the purposes of this application, the term "vibrating ingestible capsule" relates to an ingestible capsule adapted to at least intermittently vibrate, for a cumulative duration of at least one minute, in accordance with a vibration protocol of the capsule.

For the purposes of this application, the term "vibrating agitation mechanism" refers to any type of mechanism that vibrates or causes elements in its vicinity to vibrate, including a vibration motor or engine.

For the purposes of this application, the term "intermittently activated vibrating agitation mechanism" refers to a vibration engine that vibrates and is operative at certain times, and does not vibrate at other times, the activation times being selected by a control mechanism or other control unit controlling the vibration engine.

For the purposes of this application, the term "vibration protocol" relates to a protocol specifying vibration parameters of an intermittently activated vibrating agitation mechanism of a vibrating ingestible capsule. Typically, the vibration protocol relates to an activation delay for initiating vibration (e.g., a duration between "initial" activation of the capsule and the first activation of the vibration engine), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g., 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject.

For the purpose of this application, the term "activation input" relates to an input received by a control mechanism of a vibrating ingestible capsule, which causes the control mechanism of the capsule to activate itself, so as to be able to process inputs and/or to control additional components of the capsule. The activation input may be received from an element forming part of the capsule, such as a sensor sensing specific conditions in which the capsule should be activated, or from a remote source, such as a remote control mechanism, for example by way of a signal transmitted to the capsule, magnetic field applied to the capsule, specific motion applied to the capsule, or any other type of input provided to the capsule from a remote source. The activation input may be provided prior to the subject ingesting the capsule or may be provided while the capsule is traversing the GI tract of the subject.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control mechanism controlling vibration of the capsule is inactive.

For the purpose of this application, a vibrating ingestible capsule is said to be in an "operative state" when the control mechanism of the capsule is processing inputs and data, and can cause a vibrating agitation mechanism of the capsule to vibrate.

For the purpose of this application, the term "Parkinsonism" is meant to include Parkinson's disease, or symptoms of neurodegeneration associated therewith.

For the purpose of this application, the term "Parkinsonism" is meant to include progressive supranuclear palsy, or symptoms of neurodegeneration associated therewith.

For the purpose of this application, the term "Parkinsonism" is meant to include corticobasal degeneration, or symptoms of neurodegeneration associated therewith.

For the purpose of this application, the term "Parkinsonism" is meant to include multiple system atrophy, or symptoms of neurodegeneration associated therewith.

For the purpose of this application, the term "Parkinsonism" is meant to include Parkinson-plus syndromes (also known as disorders of multiple system degeneration), or symptoms of neurodegeneration associated therewith.

For the purpose of this application, the term "Parkinsonism" is meant to include any neurodegenerative disease in which the subject exhibits at least one (and typically at least two or three) of the classical features of Parkinson's disease: tremor, postural instability, and akinesia or bradykesia.

For the purpose of this application, the term "Parkinsonism" is meant to include any neurodegenerative disease in which the subject positively responds to a dopaminergic treatment.

For the purpose of this application, the term "Parkinsonism" is meant to include any neurodegenerative disease in which the particular subject positively responds to an anticholinergic treatment.

For the purpose of this application, the term "Parkinsonism" is meant to include any neurodegenerative disease in which a dopaminergic treatment is clinically utilized to treat the sufferers or subjects.

For the purpose of this application, the term "Parkinsonism" is meant to include any neurodegenerative disease in which an anticholinergic treatment is clinically utilized to treat the sufferers or subjects.

For the purpose of this application, the term "Parkinson's disease" (PD) is meant as used by those of skill in the art of neurodegenerative diseases. It is believed that PD is due to the loss of brain cells that produce dopamine. Early signs and symptoms of Parkinson's disease include at least one of tremors (or trembling), slowness of movement, body rigidity and stiffness, and gait problems.

For the purpose of this application, the term "treatment of Parkinsonism" and the like refers to at least one of: (i) delaying onset of Parkinsonism (e.g., PD); (ii) mitigating the development of Parkinsonism (e.g., PD); and (iii) managing a condition of Parkinsonism (e.g., PD).

For the purpose of this application, the term "managing a condition of", with respect to Parkinsonism and the like, is meant to include, inter alia, improving absorption of a medicament such as a medicament used in the treatment of Parkinsonism (e.g., levodopa). Such condition management may be manifested by at least one of (i) improved medicament efficacy due to the increased absorption; and (ii) reduced dosage of the medicament, due to the increased medicament absorption efficacy.

Referring now to the drawings, FIG. 1 is a schematic block diagram of a gastrointestinal treatment system 100 including a vibrating ingestible capsule 101 according to an embodiment of the present invention.

As seen in FIG. 1, gastrointestinal treatment system 100 includes vibrating ingestible capsule 101. Capsule 101 includes a capsule housing or shell 102, arranged along a longitudinal axis 103 and having disposed therein a vibrating agitation mechanism 104. A control mechanism 106, which may for example be, or include, a processor, is adapted to control operation of vibrating agitation mechanism 104, and at least one power source 108 provides power to vibrating agitation mechanism 104 and control mechanism 106.

Power source 108 may be any suitable power source, such as one or more alkaline or silver oxide batteries, primary batteries, rechargeable batteries, capacitors and/or supercapacitors.

Intermittently activated vibrating agitation mechanism 104 is adapted to have a vibration mode of operation (also termed the first mode of operation) and a rest mode of operation (also termed the second mode of operation). In the vibration mode of operation, intermittently activated vibrating agitation mechanism 104 is adapted to exert forces on capsule housing 102, such that capsule housing 102 exerts vibrations on an environment surrounding capsule 101.

In some embodiments, the capsule is in an inoperative state, until the receipt of an activation input, which causes control mechanism 106 to transition the capsule from the inoperative state to an operative state.

In some embodiments, control mechanism 106 is functionally associated with, or includes, a timing mechanism 110, powered by power source 108 and adapted to track at least one time characteristic, such as a duration that has passed since an activation input was received, or a duration that has passed since the subject ingested capsule 101.

In some embodiments, capsule 101 is devoid of any sensors for sensing an environment thereof. In some such embodiments, control mechanism 106 is adapted, in response to receipt of an activation input, to wait a predetermined delay time, and following the predetermined delay time, to activate vibrating agitation mechanism 104 to operate in said first vibration mode of operation.

In some embodiments, the predetermined delay time may be in the range of 5 minutes to 15 minutes, 5 minutes to 30 minutes, 5 minutes to 45 minutes, 5 minutes to 1 hour, 2 hours to 12 hours, 4 hours to 12 hours, 6 hours to 12 hours, 8 hours to 12 hours, 12 hours to 24 hours, 24 hours to 36 hours, 36 hours to 48 hours, or 48 hours to 72 hours.

In other embodiments, such as the embodiment illustrated in FIG. 1, capsule 101 further includes at least one sensor 112, functionally associated with control mechanism 106. The at least one sensor 112 may be adapted to sense at least one parameter within capsule 101 or in an environment of capsule 101, and may include a temperature sensor, an illumination sensor, a moisture sensor, a pressure sensor, an accelerometer, or any other suitable sensor. In some embodiments, the at least one sensor 112 is adapted to identify a specific condition in capsule 101 or in the vicinity thereof, and to provide an activation input to control mechanism 106 in response to identification of the condition. For example, in some embodiments the condition is indicative of the subject ingesting capsule 101.

For example, in some embodiments sensor 112 may include an illumination sensor, adapted to identify transition of capsule 101 from an illuminated environment (e.g. outside the human body) to a dark environment (e.g. within the human body) and to provide an activation input in response to identification of such a transition.

As another example, in some embodiments sensor 112 may include a pressure sensor adapted identify pressure applied to the capsule 101, which pressure is indicative of the capsule moving through a pharynx of the subject, and to provide an activation input in response to identification of such pressure.

As a further example, in some embodiments sensor 112 may include a temperature sensor adapted to identify transition of capsule 101 from an area with ambient temperature (e.g. outside the human body) to an area with a human body temperature and to provide an activation input in response to identification of such a transition.

As another example, in some embodiments sensor 112 may include a motion or acceleration sensor, such as an accelerometer, adapted to identify an activation motion carried out by a user on capsule 101 and to provide an activation input in response to identification of such a transition.

As a further example, in some embodiments sensor 112 may include a moisture sensor adapted to identify transition of capsule 101 from a dry area (e.g. outside the human body)

to a moist area (e.g. within the human body) and to provide an activation input in response to identification of such a transition.

In some embodiments, system 100 further includes a control unit 120, which may be remote from capsule 101, and which is adapted to provide one or more inputs to the capsule. In some such embodiments, capsule 101 further includes a remote input receiving mechanism 116, functionally associated with control mechanism 106, and adapted to receive inputs from an input providing mechanism 122 of control unit 120.

In some embodiments, control unit 120 may further include a timing mechanism 126, adapted to track at least one time characteristic, such as a duration that has passed since a control instruction was provided to capsule 101.

In some embodiments, control unit 120 may further include a user input receiver 128, such as a keyboard, touch screen, or touch pad, adapted to receive input from a user, such as the subject, a medical professional treating the subject, or a caregiver of the subject.

Control unit 120 may be any suitable type of control unit. In some embodiments, control unit may be a suitably configured smart phone or a tablet computer.

In some such embodiments, control unit 120 may provide inputs to capsule 101 by remotely transmitting the inputs from input providing mechanism 122 to remote input receiving mechanism 116, for example using a short range wireless communication method, such as radio frequency (RF) communication or Bluetooth® communication. One example of such a mechanism for providing input to a capsule is described in U.S. patent application Ser. No. 15/132,039 filed Apr. 18, 2016 and entitled "IN VIVO DEVICE AND METHOD OF USING THE SAME", which is incorporated by reference for all purposes as if fully set forth herein.

In some embodiments, control unit 120 is adapted to provide the activation input to control mechanism 106 of capsule 101. In some such embodiments, control unit 120 provides the activation input prior to the subject ingesting capsule 101, whereas in other embodiments control unit 120 provides the activation input following ingestion of capsule 101 by the subject.

Relating to the characteristics of vibrating agitation mechanism 104, the vibrating agitation mechanism may be any suitable mechanism that can be intermittently activated and can apply suitable forces onto capsule housing 102.

In some embodiments, intermittently activated vibrating agitation mechanism 104 may include a radial agitation mechanism adapted to exert radial forces on capsule housing 102, in a radial direction with respect to the longitudinal axis of housing 102. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitation mechanism 104 may include an axial agitation mechanism adapted to exert radial forces on the capsule housing 102, in an axial direction with respect to a longitudinal axis of housing 102. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitation mechanism 104 on capsule housing 102 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitation mechanism 104.

In some embodiments, the intermittently activated vibrating agitation mechanism 104 may include a magnet mounted onto a rotor adapted to exert a magnetic field as well as radial forces on capsule housing 102. For example, such a magnetic vibration agitation mechanism is described in U.S. patent application Ser. No. 15/058,216 filed on Mar. 2, 2016 and entitled "PHYSIOTHERAPY DEVICE AND METHOD FOR CONTROLLING THE PHYSIOTHERAPY DEVICE", which is incorporated by reference for all purposes as if fully set forth herein.

In some embodiments, housing 102 may include first and second members, and vibrating agitation mechanism 104 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In the vibrating mode of operation, intermittently activated vibrating agitation mechanism 104 is adapted to have a plurality of vibration cycles, where each cycle includes a vibration duration followed by a repose duration. Forces are exerted by the vibrating agitation mechanism 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitation mechanism 104 is operative in the vibration mode for a first duration, for example 30 minutes, then does have any vibration cycles for a second duration, for example 1 hour, and then is operative in the vibration mode and has vibration cycles for a third duration, for example two hours. The cumulative duration relates to the sum of all durations during which vibrating agitation mechanism 104 was operative in the vibration mode and included vibration cycles, including the vibration duration and the repose duration of the vibration cycle.

In some embodiments, vibrating agitation mechanism 104 is configured to exert forces on the capsule housing 102, such that a net force exerted by the capsule housing 102 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitation mechanism 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitation mechanism.

It will be further appreciated that a specific capsule may be controlled by the control mechanism such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Control mechanism 106 is adapted to control the operation of intermittently activated vibrating agitation mechanism 104. Such control may include control of any one or more of the force applied by the vibrating agitation mechanism, the vibrational frequency reached, the times in which vibrating agitation mechanism 104 operates in the vibration mode of operation, the vibration duration of each vibration cycle, the repose duration of each vibration cycle, the vibration cycle duration, and cumulative vibration duration of the vibrating agitation mechanisms.

In some embodiments, control mechanism 106 is adapted to receive information relating to the desired vibration protocol from control unit 120, prior to ingestion of the capsule or to activation thereof, or during the capsule's traversal of the subject's GI tract. For example, the information may be remotely transmitted from control unit 120 to control mechanism 106, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes a desired number of vibration cycles, a desired vibration duration in each vibration cycle, a desired repose duration in each vibration cycle, a desired cumulative vibration duration, and the like.

In some embodiments, control mechanism 106 is adapted to control vibrating agitation mechanism 104 so that the capsule applies forces to an environment thereof to effect a mechanical stimulation of the wall of the gastrointestinal tract of the subject at the predetermined time(s).

Reference is now additionally made to FIG. 2, which is a schematic flowchart of a method for using a vibrating gastrointestinal capsule in the treatment of Parkinsonism in a subject, according to the present invention, the treatment being based on use of a gastrointestinal treatment system including (or consisting of) a vibrating ingestible capsule, such as capsule 101 of system 100 of FIG. 1.

As seen at step 200, vibrating gastrointestinal capsule is provided. The vibrating gastrointestinal capsule may have, as described with respect to FIG. 1, a housing; a vibrating agitation mechanism adapted such that, in a first vibrating mode of operation, the housing exerts vibrations on an environment surrounding the vibrating gastrointestinal capsule; and a power supply disposed within the housing and adapted to power the vibrating agitation mechanism. Typically, the capsule includes an on-board control mechanism adapted to control or activate the vibrating agitation mechanism. The control mechanism may form a component of such a vibrating agitation mechanism.

At step 204, the vibrating gastrointestinal capsule is ingested by the subject.

As shown, step 206A includes activating or controlling the vibrating agitation mechanism within the capsule such that at least a portion of the first vibrating mode of operation occurs within a portion of a gastrointestinal tract of the subject. This portion consists, at most, of the stomach, small intestine, and large intestine. More typically, however, for the treatment of Parkinsonism, this portion consists, at most, of the stomach and small intestine.

Additionally or alternatively, the vibrating agitation mechanism within the capsule may be activated or controlled (step 206B) such that at least a portion of the first vibrating mode of operation occurs within 6 hours or within 5 hours, more typically within 4.5 hours or within 4 hours, and yet more typically, within 3.5 hours, within 3 hours, within 2.5 hours, within 2 hours, within 1.5 hours, within 1 hour, or within 0.5 hours of the ingesting of the vibrating gastrointestinal capsule, or from attaining the operative state (step 202), as described hereinabove.

This may be done, by way of example, such that the vibrations will be effected within the stomach and/or small intestine, so as to treat the Parkinsonism.

The capsule may be pre-programmed with a vibration protocol. This protocol may include, by way of example, a particular or pre-determined activation time following ingestion, in which the capsule is transitioned from an inoperative state to an operative state. Alternatively or additionally, the capsule may receive an activation input in an active fashion (e.g., from an external controller via RF) or in a passive fashion (e.g., a signal from a sensor to the on-board controller). It will be appreciated that step 202 may be performed after ingestion of the capsule by the subject (e.g., in the case of external control via RF).

In some embodiments, control mechanism 106 may optionally receive a desired vibration protocol for the subject.

In some embodiments, providing of the predetermined time(s) at step 202 and/or providing the desired vibration protocol for the subject at step 204 occurs at the time of manufacturing of the capsule, for example by pre-programming the time into the control mechanism.

In some embodiments, providing of the predetermined time(s) at step 202 and/or providing the desired vibration protocol for the subject at step 204 may be effected by a control unit, such as control unit 120 of FIG. 1.

The programming of the vibration protocol may include remotely transmitting the desired vibration protocol from control unit 120 to control mechanism 106, for example using a short-range wireless communication method. In some embodiments, the desired vibration protocol is transmitted as a list of vibration parameters for effecting the vibration protocol. In some embodiments, the desired vibration protocol is transmitted as executable code for effecting the vibration protocol.

As discussed hereinabove, in some embodiments the activation input may be received from the control unit 120 or from sensors within the capsule sensing that the capsule has been ingested or that a user has carried out an activation motion with the capsule.

Substantially as described hereinabove, the capsule may be activated prior to the user ingesting the capsule at step 204, for example by a signal from the control unit or by the user carrying out an activation motion. In other embodiments, the activation input is provided at the time of ingestion or immediately thereafter, for example by sensors sensing a change in the environment of the capsule due to its ingestion, as described at length hereinabove. In yet other embodiments, the activation input may be provided remotely when the capsule is already in the body of the subject, for example by remote communication from control module 120.

Following activation of capsule 101, or together therewith, capsule 101 is ingested by the subject, and begins to travel through the gastrointestinal tract of the subject, as evident from step 204.

Operation of vibrating agitation mechanism 104 in the vibrating mode of operation at step 206A or 206B effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

The importance of the gut-brain axis in prevention or improvement of ailments of the GI tract, such as irritable bowel syndrome (IBS) and chronic idiopathic constipation (CIC) has been shown, for example, in *"Irritable bowel syndrome, the microbiota and the gut-brain axis"* to Raskov et al (published in Gut Microbes. 2016; 7(5): 365-383), which is incorporated by reference as if fully set forth herein. Raskov et al show that the bidirectional neurohumoral integrated communication between the microbiota and the autonomous nervous system, which is called the gut-brain-axis, integrates brain and GI functions, such as gut motility, appetite and weight. Raskov et al further state that "the gut-brain-axis has a central function in the perpetuation of irritable bowel syndrome and the microbiota plays a critical role".

The connection between ailments of the GI tract, such as IBS and CIC, and Parkinson's disease or Parkinsonism, has been shown, for example in "A Role for Neuronal Alpha-Synuclein in Gastrointestinal Immunity" to Stolzenberg et al (J Innate Immun 2017; 9:456-463), and in "Medical records documentation of constipation preceding Parkinson disease" to Savica et al (Neurology, Nov. 24, 2009; 73(21)), which are both incorporated by reference as if fully set forth herein. According to the findings of Stolzenberg et al and of Savica et al, chronic gastrointestinal ailments may be a trigger, or a precursor, of Parkinson's disease, or of parkinsonism. Such chronic ailments of the GI tract may occur as early as 20 or more years before onset of motor symptoms, and are associated with increased risk of Parkinson's disease.

Without wishing to be bound by theory, Applicants believe that stimulation of the wall of the gastrointestinal tract at step 206A or 206B activates the gut-brain axis to indicate to the brain that gut function is required, thereby causing the brain to trigger the GI tract to better stimulate contractions and peristalsis in the GI tract, and specifically in the large intestine and in the colon. Given the prevalent evidence regarding the association of the gut-brain axis in development and deterioration of Parkinson's disease and its neurodegenerative symptoms, such activation of the gut-brain axis and improvement of GI function improves, and/or delays symptoms of, Parkinson's disease and Parkinsonism.

A treatment session as defined in steps 200 to 206A or 206B may be repeatedly administered to the subject as specified in the treatment protocol for the subject. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks. In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of using a vibrating gastrointestinal capsule in the treatment of Parkinsonism in a subject, the method comprising:
   (a) providing the vibrating gastrointestinal capsule, the vibrating gastrointestinal capsule having:
      a housing;
      a vibrating agitation mechanism adapted such that, in a first vibrating mode of operation, said housing exerts vibrations on an environment surrounding the vibrating gastrointestinal capsule; and
      a power supply disposed within said housing and adapted to power said vibrating agitation mechanism,
      wherein the vibrating agitation mechanism is adapted to exert forces on said housing to attain a housing vibrational frequency within a range of 10 Hz to 650 Hz;
   (b) ingesting the vibrating gastrointestinal capsule, by the subject;
   (c) controlling or activating said vibrating agitation mechanism such that at least a portion of said first vibrating mode of operation occurs within a portion of a gastrointestinal tract of the subject, said portion consisting at most of a stomach, a small intestine, and large intestine,
      wherein mechanical stimulation applied to a wall of the portion of the gastrointestinal tract, by said vibrating gastrointestinal capsule operating in said first vibrating mode of operation, is the primary treatment of the Parkinsonism in the subject.

2. The method of claim 1, wherein said portion of said gastrointestinal tract consists at most of said stomach and said small intestine.

3. The method of claim 1, wherein the vibrating gastrointestinal capsule includes, or is associated with, a control mechanism adapted to activate said vibrating agitation mechanism to operate in said first vibrating mode of operation.

4. The method of claim 1, wherein the treatment of Parkinsonism is, or includes, delaying an onset of Parkinsonism.

5. The method of claim 1, wherein the treatment of Parkinsonism is, or includes, mitigating or retarding a development of Parkinsonism.

6. The method of claim 1, wherein the treatment of Parkinsonism is, or includes, managing a condition of Parkinsonism.

7. The method of claim 1, wherein the treatment of Parkinsonism is the treatment of Parkinson's disease.

8. The method of claim 1, wherein said first vibrating mode of operation is effected within said portion of said gastrointestinal tract so as to stimulate the enteric nervous system of the subject.

9. The method of claim 1, wherein said first vibrating mode of operation is effected within said portion of said gastrointestinal tract so as to induce at least one peristaltic wave in a wall of said gastrointestinal tract.

10. The method of claim 1, wherein said first vibrating mode of operation is effected within said portion of said gastrointestinal tract so as to increase peristalsis in a wall of said gastrointestinal tract.

11. The method of claim 10, wherein said increasing of said peristalsis is effected so as to stimulate the enteric nervous system of the subject.

12. The method of claim 1, further comprising diagnosing a pre-disposition to Parkinsonism or Parkinson's disease in the subject, wherein the treatment of Parkinsonism is, or includes, delaying an onset of Parkinsonism.

13. The method of claim 1, wherein the capsule further includes a control mechanism adapted, in response to receipt of an activation input, to activate said vibrating agitation mechanism to operate in said first vibrating mode of operation.

14. The method of claim 13, wherein the capsule further includes at least one sensor adapted to provide said activation input.

15. The method of claim 13, wherein said receipt of said activation input comprises receiving said activation input from a control unit remote from said gastrointestinal capsule.

16. The method of claim 1, wherein said activating comprises activating said vibrating agitation mechanism to operate in said first vibrating mode of operation for a cumulative duration in the range of 1 hour to 12 hours.

17. A method of using a vibrating gastrointestinal capsule in the treatment of Parkinsonism in a subject, the method comprising:
   (a) providing the vibrating gastrointestinal capsule, the vibrating gastrointestinal capsule having:
      a housing;
      a vibrating agitation mechanism adapted such that, in a first vibrating mode of operation, said housing exerts vibrations on an environment surrounding the vibrating gastrointestinal capsule; and
      a power supply disposed within said housing and adapted to power said vibrating agitation mechanism,
      wherein the vibrating agitation mechanism is adapted to exert forces on said housing to attain a housing vibrational frequency within a range of 10 Hz to 650 Hz;
   (b) ingesting the vibrating gastrointestinal capsule, by the subject;
   (c) activating said vibrating agitation mechanism such that at least a portion of said first vibrating mode of operation occurs within 6 hours, within 5 hours, within 4.5 hours, within 4 hours, within 3.5 hours, within 3 hours, within 2.5 hours, within 2 hours, within 1.5 hours, within 1 hour, or within 0.5 hours of said ingesting of the vibrating gastrointestinal capsule,
      wherein mechanical stimulation applied to a wall of the portion of the gastrointestinal tract, by said vibrating gastrointestinal capsule operating in said first vibrating mode of operation, is the primary treatment of the Parkinsonism in the subject.

18. The method of claim 17, wherein said activating comprises activating said vibrating agitation mechanism to operate in said first vibrating mode of operation for a cumulative duration in the range of 1 hour to 12 hours.

* * * * *